(12) United States Patent
Sato et al.

(10) Patent No.: US 6,418,782 B1
(45) Date of Patent: Jul. 16, 2002

(54) GAS CONCENTRATION SENSOR (75) Inventors: Yoshikuni Sato, Aichi; Noboru Ishida, Gifu; Hideki Ishikawa, Aichi; Takafumi Oshima, Aichi; Yasushi Sato, Aichi, all of (JP)

(73) Assignee: NGK Spark Plug Co., Ltd, Aichi (JP)

( * ) Notice: Subject to any disclaimer, the term of this patent is extended or adjusted under 35 U.S.C. 154(b) by 0 days.

(21) Appl. No.: 09/480,663

(22) Filed: Jan. 11, 2000

(30) Foreign Application Priority Data

Jan. 11, 1999 (JP) .......................................... 11-004286

(51) Int. Cl.$^7$ ............................................. G01N 29/02
(52) U.S. Cl. ........................................ 73/24.01; 73/597
(58) Field of Search .......................... 73/24.01, 861.25, 73/861.27, 861.29, 861.28, 861.31, 597, 598, 302; 702/190

(56) References Cited

U.S. PATENT DOCUMENTS

| | | | |
|---|---|---|---|
| 4,112,756 A | * 9/1978 | MacLennan et al. | 73/597 |
| 4,787,252 A | 11/1988 | Jacobson et al. | 73/861.28 |
| 5,042,303 A | * 8/1991 | Geluk et al. | 73/602 |
| 5,178,018 A | * 1/1993 | Gill | 73/861.28 |
| 5,581,014 A | * 12/1996 | Douglas | 73/24.01 |
| 5,808,200 A | * 9/1998 | Dam | 73/861.29 |
| 6,009,380 A | * 12/1999 | Vecchio et al. | 73/597 |
| 6,116,080 A | * 9/2000 | Logue et al. | 73/597 |

FOREIGN PATENT DOCUMENTS

| JP | 44-30915 | 12/1969 | |
|---|---|---|---|
| JP | 8-105865 | 4/1996 | G01N/29/18 |

OTHER PUBLICATIONS

M. Habaguchi et al, "Gasoline Vapor Concentration Sensor–On Board Measurement by Ultrasonic Pulse–", Proceedings for Society of Automotive Engineers of Japan 955, 1995–9 (translation).
M. Sultan et al, "Closed Loop Canister Purge Control System", Sae Technical Paper Series 980206.

* cited by examiner

*Primary Examiner*—Hezron Williams
*Assistant Examiner*—Michael Cygan
(74) *Attorney, Agent, or Firm*—Sughrue Mion, PLLC (57) ABSTRACT

When a sensor has deteriorated, the propagation time T1' of a first reflection wave becomes greater than the propagation time T1 of a first reflection wave as measured in a new sensor. If measurement of the concentration of a specific gas is based on the propagation time T1 of the first reflection wave as measured in the new sensor, gas concentration cannot be determined accurately. By contrast, a reflection wave other than the first reflection wave (for example, a second reflection wave) is merely reflected off the surface of the ultrasonic element and is not affected by the internal structure of the ultrasonic element. Therefore, even when the sensor is deteriorated, the propagation time T2, T2' of the second reflection wave exhibits less variation and is less susceptible to deterioration of the sensor. Therefore, the concentration of a specific gas is determined on the basis of the propagation time of the second reflection wave, which is less susceptible to deterioration of the sensor, instead of the propagation time of the first reflection wave, which is more susceptible to deterioration of the sensor. Thus, gas concentration can be measured accurately.

3 Claims, 10 Drawing Sheets

Fig. 1.

Fig.2(a).
Gas Concentration Sensor 25

Fig.2(b).
Ultrasonic Transmitter-Receiver Elements 32

Transmitted waveform

Fig.11(b).

Received waveform

Threshold level

Comparator output

Arrival point of ultrasonic wave

GAS CONCENTRATION SENSOR

BACKGROUND OF THE INVENTION

1. Field of the Invention

The present invention relates to a gas concentration sensor for measuring the concentration of combustible gas, such as vaporized fuel, contained in, for example, intake air to be supplied into an intake pipe of, for example, an internal combustion engine.

2. Description of the Related Art

Conventionally, a fuel supply system for supply of fuel from a fuel tank to an engine includes a first supply system which functions in the following manner. Fuel is pumped from the fuel tank by means of a fuel pump and is then sent to an injector through a fuel pipe.

The fuel supply system further includes a second supply system which functions in the following manner. Vaporized fuel generated within the fuel tank is temporarily adsorbed by a canister. Accumulated vaporized fuel is purged from the canister and is sent as purge gas to an intake pipe.

Accordingly, in addition to fuel injected from the injector, vaporized fuel, such as purge gas, is burned within a cylinder of the engine (hereinafter vaporized fuel is referred to merely as purge gas).

When, as a result of supply to the engine of purge gas in addition to injected fuel, an air-fuel ratio deviates from a theoretical value, the purification capability of a catalyst with respect to CO, HC, and NOx lowers considerably. As a result, CO, HC, and NOx contents of exhaust gas increase.

Accordingly, in order to use purge gas as a portion of main fuel for combustion, for example, at engine start-up, particularly when the catalyst is inactive, optimum control of purge gas supply through highly accurate measurement of purge gas concentration is very important.

A sensor for measuring purge gas concentration may utilize, for example, ultrasonic waves (ultrasonic sensor). Such an ultrasonic sensor has been developed, but a satisfactory ultrasonic sensor has not yet been developed.

Such an ultrasonic sensor detects concentration of purge gas on the basis of propagation time of a transmitted ultrasonic wave. However, such an ultrasonic sensor has the following problem. When a material constituting an ultrasonic element of the ultrasonic sensor deteriorates over time, the characteristics of the ultrasonic element change, so that the propagation time of an ultrasonic wave to be measured changes. Therefore, it has been difficult to accurately measure concentration of purge gas.

Accordingly, there has been a problem that concentration of purge gas is very difficult to control accurately on the basis of results of measurement regarding the concentration of purge gas.

The present invention has been achieved to solve the above problems, and an object of the invention is to provide a gas concentration sensor capable of accurately measuring the concentration of a specific gas, such as purge gas.

SUMMARY OF THE INVENTION

To achieve the above object, the invention of claim 1 provides a gas concentration sensor which detects gas concentration of a specific gas in a gas under measurement. The gas concentration sensor comprises an ultrasonic element for transmitting an ultrasonic wave to a reflection surface, which is a predetermined distance away from the ultrasonic element, via a space into which the gas under measurement is supplied. The ultrasonic element is caused to transmit an ultrasonic wave toward the reflection surface. The ultrasonic wave reflects off the reflection surface to thereby become a first reflection wave, the ultrasonic element reflects the first reflection wave so that the first reflection wave is again reflected off the reflection surface. Concentration of the specific gas is detected on the basis of a propagation time of a reflection wave other than the first reflection wave.

During measurement of concentration of a specific gas by use of a so-called ultrasonic sensor, an ultrasonic wave is transmitted into a gas under measurement, a time period until receipt of the transmitted ultrasonic wave or a reflection wave from a reflection surface is measured; and the concentration of the specific gas is obtained on the basis of the time period (propagation time).

This technique utilizes a characteristic of ultrasonic waves that, as shown in FIG. 4, their propagation time changes depending on the concentration of a specific gas contained in a gas under measurement.

Figure 8:
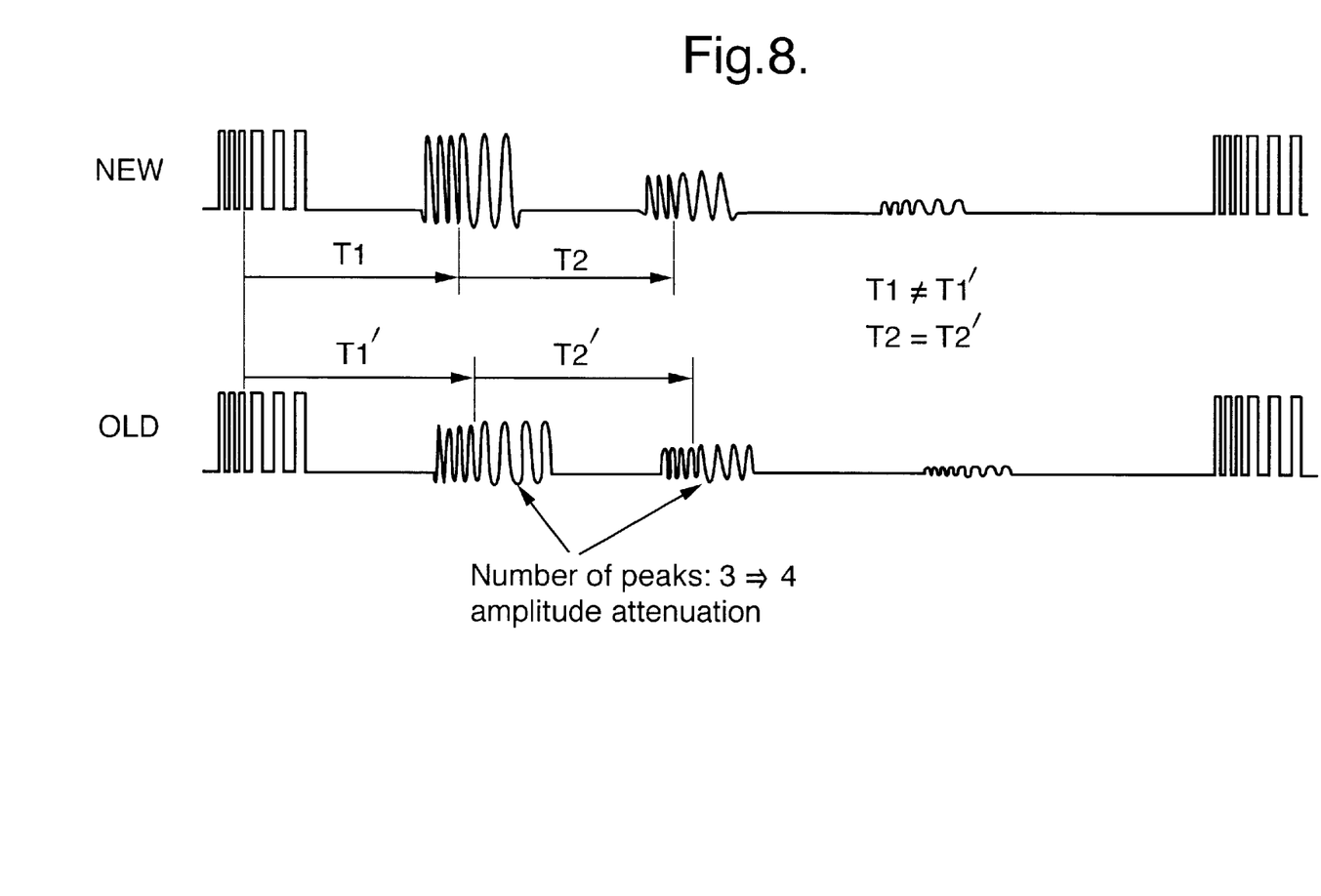
FIG. 8 is a timing chart showing a transmitted/received waveform of an ultrasonic wave in each of new and deteriorated sensors.

However, in the case where characteristics of a molded material of the ultrasonic element have changed due to time-course deterioration, as shown in FIG. 8, the propagation time T1' of the first reflection wave becomes greater than the propagation time T1 of the first reflection wave as measured in a new sensor. If measurement of the concentration of a specific gas is based on the propagation time T1 of the first reflection wave as measured in the new sensor, gas concentration cannot be determined accurately. By contrast, a reflection wave other than the first reflection wave (for example, a second reflection wave) is merely reflected off the surface of the ultrasonic element and is not affected by the internal structure of the ultrasonic element. As shown in FIG. 8, even when the sensor is deteriorated, the propagation time T2, T2' of, for example, the second reflection wave exhibits less variation and is less susceptible to deterioration of the sensor than is the propagation time T1 of the first reflection wave.

Therefore, in the present invention, the concentration of a specific gas is determined on the basis of the propagation time of the second or later reflection wave, which is less susceptible to deterioration of the sensor, instead of the propagation time of the first reflection wave, which is more susceptible to deterioration of the sensor.

Thus, gas concentration can be measured accurately. On the basis of accurately measured gas concentration, gas concentration can be adjusted accurately, whereby, for example, control of air-fuel ratio can be performed favorably.

Preferably the gas concentration sensor is further characterized in that the first reflection wave reflected off the reflection surface and the second reflection wave-which results from reflection of the first reflection wave off the reflection surface-are detected; and a time period between the arrival of the first reflection wave and the arrival of the second reflection wave is measured in order to detect the gas concentration of the specific gas.

Accordingly, in order to measure the concentration of the specific gas in a gas under measurement, the ultrasonic element is caused to transmit an ultrasonic wave toward the reflection surface, which is a predetermined distance away from the ultrasonic element, via a space into which the gas under measurement is supplied. The first reflection wave—which results from reflection of the transmitted reflection wave on the reflection surface—is first detected. Then, the second reflection wave—which results from reflection of the first reflection wave off the ultrasonic element and then off the reflection surface—is detected. Subsequently, a time period between the arrival of the first reflection wave and the arrival of the second reflection wave (i.e., the propagation time of the second reflection wave) is measured in order to detect the gas concentration of the specific gas.

As described above, even when the sensor deteriorates, the propagation time of the second reflection wave hardly changes. Therefore, the propagation time of the second reflection wave is less susceptible to deterioration of the sensor than is the propagation time of the first reflection wave. Further, since the degree of attenuation of the second reflection wave is smaller than that of later or higher-order reflection waves, the received waveform of the second reflection wave can be detected clearly.

Therefore, in this preferred aspect of the invention, the concentration of the specific gas is determined on the basis of the propagation time of the second reflection wave, which is less susceptible to deterioration of the sensor, instead of the propagation time of the first reflection wave, which is more susceptible to deterioration of the sensor. That is, the concentration of the specific gas is determined through measurement of a time period between the arrival of the first reflection wave and the arrival of the second reflection wave.

Thus, gas concentration can be measured more accurately. On the basis of accurately measured gas concentration, gas concentration can be adjusted accurately, whereby, for example, control of air-fuel ratio can be performed favorably.

Preferably, the gas concentration sensor is further characterized in that a first arrival time between a time of transmission of the ultrasonic wave and the arrival of the first reflection wave and a second arrival time between the time of transmission of the ultrasonic wave and the arrival of the second reflection wave are measured; and the gas concentration is detected on the basis of the difference between the first and second arrival times.

Figure 7A:
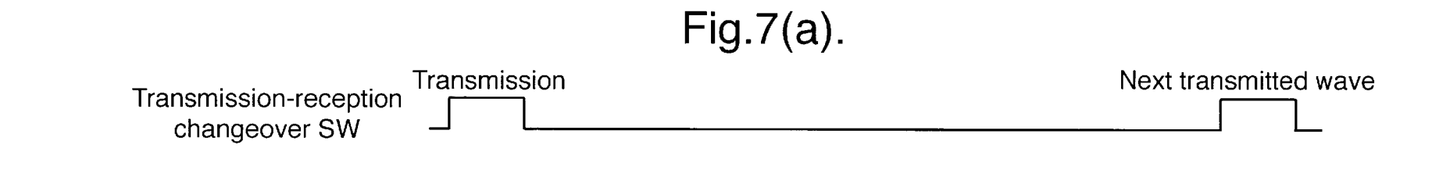
FIGS. 7(a), (b) and (c) are timing charts, wherein (a) is a timing chart showing a signal emitted from a transmission-reception changeover switch, (b) is a timing chart showing a transmitted/received waveform, and (c) is a timing chart showing a comparator output.
Figure 7B:
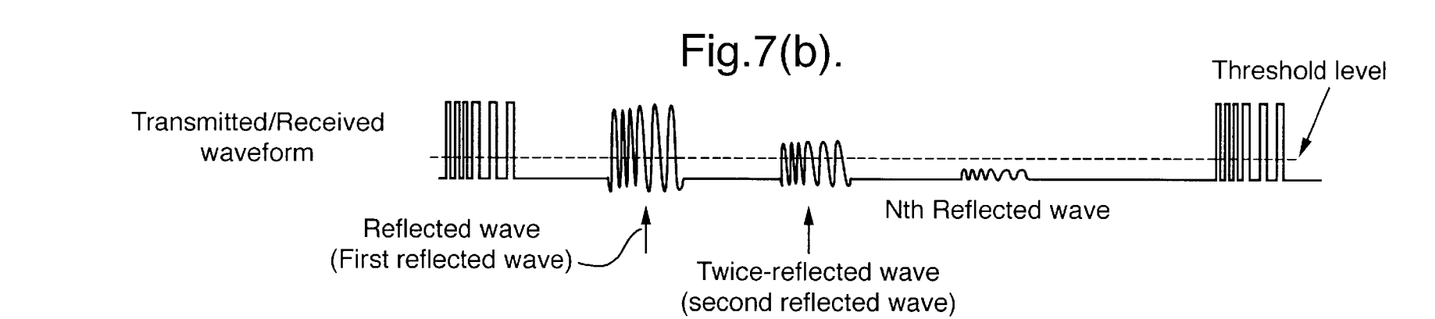
Figure 7C:
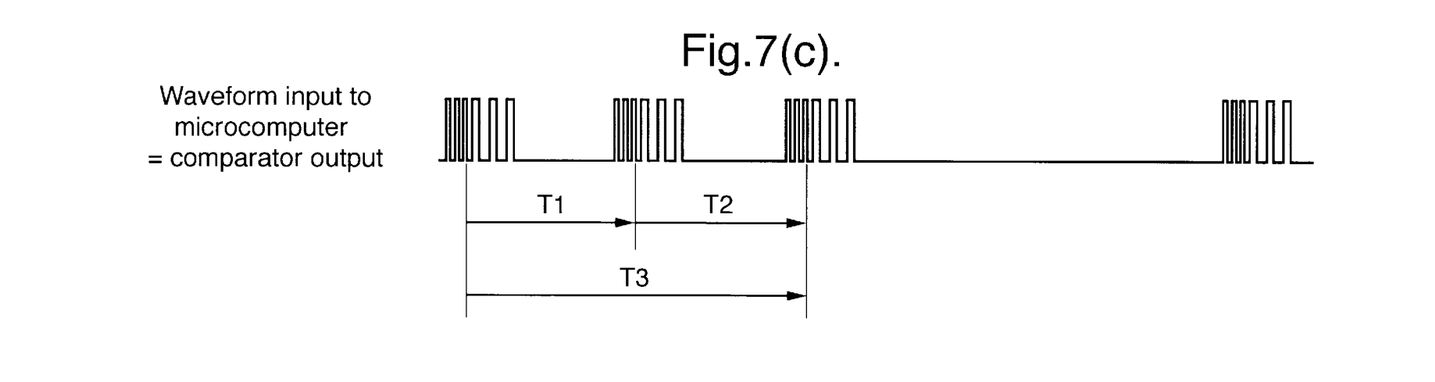

According to this preferred aspect, a first arrival time between a time of transmission of the ultrasonic wave and the arrival of the first reflection wave and a second arrival time between the time of transmission of the ultrasonic wave and the arrival of the second reflection wave are measured. For example, as shown in FIG. 7, a second arrival time (T3) and a first arrival time (T1) is measured. Subsequently, the difference (T2) between the two time periods is calculated. Since the difference represents the propagation time of the second reflection wave, the gas concentration is detected on the basis of the difference.

Preferably, the gas concentration sensor is further characterized in that the measurement of each time period is performed when the level of a received signal of the ultrasonic wave exceeds a predetermined threshold.

The invention according to this preferred aspect exemplifies the timing for measuring a propagation time or arrival time of an ultrasonic wave. Accordingly, a point in time when the level of a received signal of the ultrasonic wave exceeds a predetermined threshold is used as a timing for measuring a propagation time or arrival time of an ultrasonic wave. Thus, it becomes possible to measure a propagation time or arrival time of an ultrasonic wave through use of simple means.

The term "propagation time" refers to a time period required for propagation of an ultrasonic wave over a certain distance. The term "arrival time" refers to a time period between a measurement start timing serving as a reference and a timing at which a certain reflection wave arrives at the sensor. For the first reflection wave, the propagation time and the arrival time become the same.

Preferably, the gas concentration sensor is further characterized in that an ultrasonic wave involving at least two frequency components is transmitted; and a propagation time required for propagation of the ultrasonic wave over a predetermined distance is measured through utilization of the modulation point present in the ultrasonic wave in order to detect the concentration of the specific gas.

This preferred aspect of the invention exemplifies the timing for measuring a propagation time of an ultrasonic wave. As shown in FIG. 7, an ultrasonic wave having at least two frequency components is transmitted. Subsequently, a time period (T1) between the modulation point in the transmitted wave and the modulation point in the first reflection wave, and a time period (T3) between the modulation point in the transmitted wave and the modulation point in the second reflection wave are measured. This enables precise measurement of the propagation time of the ultrasonic wave without regard for the degree of intensity of a signal.

Preferably, the gas concentration sensor is further characterized in that an ultrasonic wave involving at least one antiphase component is transmitted; and a propagation time required for propagation of the ultrasonic wave over a predetermined distance is measured through utilization of the antiphase point present in the ultrasonic wave in order to detect the concentration of the specific gas.

This preferred aspect of the invention exemplifies the timing for measuring a propagation time of an ultrasonic wave. As shown in FIG. 10, an ultrasonic wave having at least one antiphase point is transmitted. Subsequently, a propagation time which the ultrasonic wave requires to propagate over a predetermined distance is measured through utilization of the antiphase point present in the ultrasonic wave. Thus, without performance of frequency modulation, precise measurement of the propagation time of the ultrasonic wave can be performed without regard for the degree of intensity of a signal.

Preferably, the gas concentration sensor is further characterized in that the specific gas is vaporized fuel for use with an internal combustion engine.

This preferred aspect of the invention specifies a specific gas to be measured by the gas concentration sensor. The gas concentration sensor is intended to measure the concentration of vaporized fuel, such as purge gas. Since fuel gas concentration can be measured accurately, an air-fuel ratio, etc. can be controlled favorably.

Embodiments of the invention will now be described, by way of example only, with reference to the accompanying drawings.

Reference numerals in the drawings identify items as follows:

1: engine
2: intake pipe
6: injector
7: exhaust pipe
8: oxygen sensor
11: gasoline tank
14: canister
17: purge valve
21, 22, 23, 24, 25: gas concentration sensor
26: electronic control unit (ECU)
32: ultrasonic transmitter-receiver element (ultrasonic elements)
33: reflection surface
34: measurement chamber

DESCRIPTION OF THE PREFERRED EMBODIMENTS

First Embodiment

A gas concentration sensor according to a first embodiment utilizes an ultrasonic wave so as to measure vaporized fuel concentration.

a) First, the configuration of a system which employs a gas concentration sensor of the present embodiment will be described.

Figure 1:
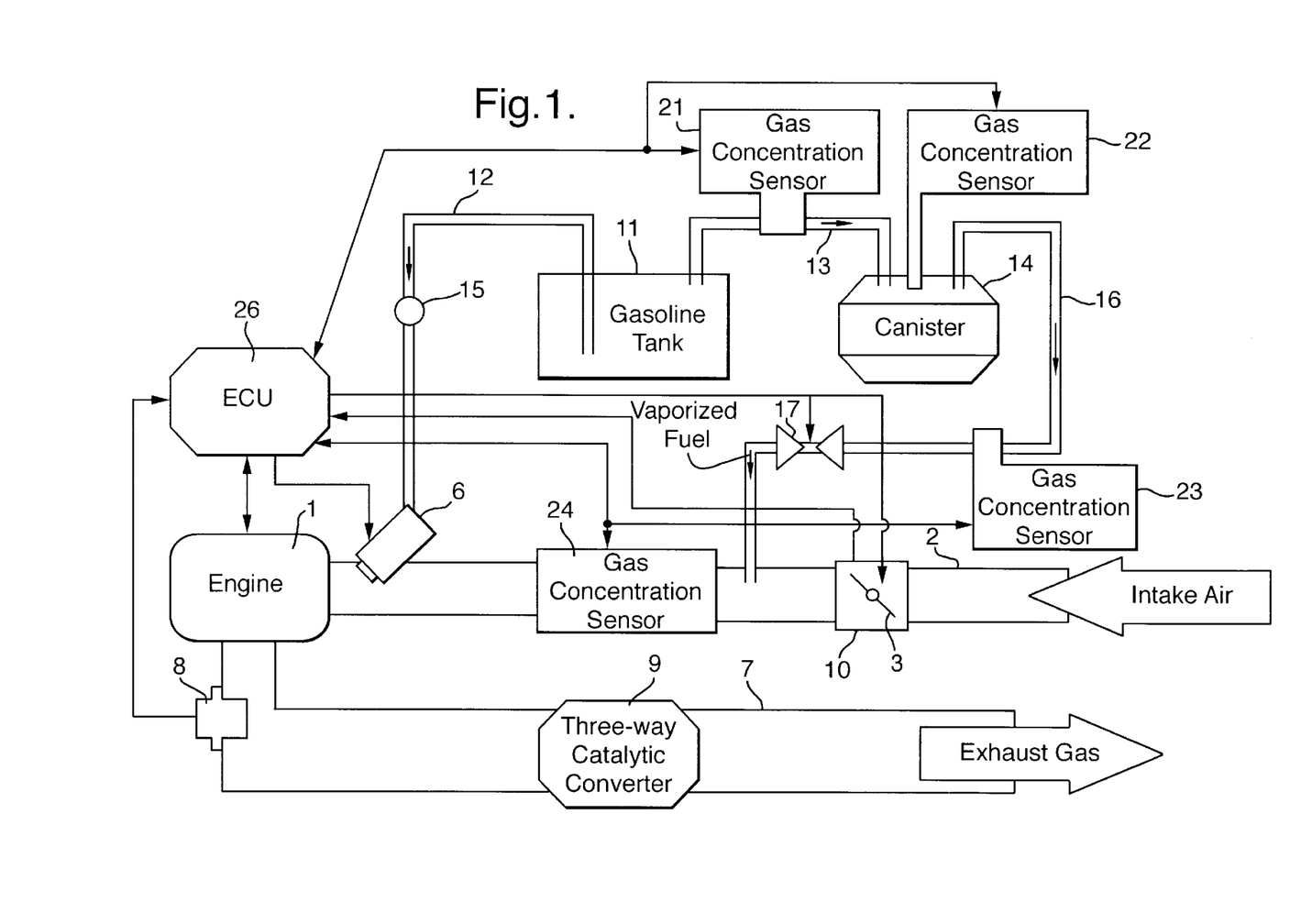
FIG. 1 is a system diagram showing an entire system which includes a controller for gas concentration sensors according to a first embodiment of the present invention.

FIG. 1 is a diagram showing a system configuration including gas concentration sensors.

As shown in FIG. 1, a throttle valve 3 for regulating intake air volume, a fourth gas concentration sensor 24 for detecting purge gas concentration, and an injector 6 for injecting fuel, from upstream side to downstream side, are disposed on an intake pipe 2 of an engine 1.

An oxygen sensor (full-range-type air-fuel ratio sensor) 8 for detecting oxygen concentration in exhaust gas and a three-way catalytic converter 9 for purifying exhaust gas, from upstream side to downstream side, are disposed on an exhaust pipe 7 of the engine 1.

A path for supplying fuel to the engine 1 includes a first supply system for supplying liquid fuel and a second supply system for supplying gas fuel.

In the first supply system, a gasoline tank 11 is connected to the injector 6 via a first supply path 12 and a fuel pump 15. Fuel is supplied, through the first supply path 12, from the gasoline tank 11 to the injector 6 by means of the fuel pump 15. Then, fuel is injected into the intake pipe 2 from the injector 6.

In the second supply system, the gasoline tank 11 is connected to a canister 14 via a second supply path 13. The canister 14 is connected, via a third supply path 16 and a purge valve 17, to a portion of the intake pipe 2 extending between the throttle valve 3 and the fourth gas concentration sensor 24.

In order to detect vaporized fuel concentration, a first gas concentration sensor 21 is disposed on the second supply path 13; a second gas concentration sensor 22 is disposed on the canister 14; and a third gas concentration sensor 23 is disposed on the third supply path 16 extending between the canister 14 and the purge valve 17. Alternatively, any one of the first through third gas concentration sensors 21 to 23 may be disposed. Vaporized fuel which is purged (ejected through evaporation) from the canister 14 is called purge gas.

Fuel which has evaporated from the gasoline tank 11 is once adsorbed by the canister 14. Outside air is introduced as appropriate into the canister 14 to thereby purge fuel. The thus-purged vaporized fuel (purge gas) undergoes flow regulation in the purge valve 17 and is then supplied into a portion of the intake pipe 2 extending between the throttle valve 3 and the fourth gas concentration sensor 24.

This system employs an electronic control unit (ECU) 26 in order to control purge gas supply and air-fuel ratio. The ECU 26 receives signals from various sensors, such as the first through fourth gas concentration sensors 21 to 24 (hereinafter generically referred to as a gas concentration sensor 25), the oxygen sensor 8, and an air flowmeter 10. The ECU 26 outputs control signals to various actuators, such as the purge valve 17, the throttle valve 3, and the injector 6. The ECU 26 also outputs a control signal, such as an on-off signal, to the gas concentration sensor 25.

b) The structure and basic principle of the gas concentration sensor 25 of the present embodiment will next be described.

(1) First, the structure of the gas concentration sensor 25 will be described.

The gas concentration sensor 25 is an ultrasonic gas concentration sensor which generates an ultrasonic wave through utilization of a piezoelectric element. The gas concentration sensor 25 employs an ultrasonic transmitter-receiver element (element assembly) which transmits and receives an ultrasonic wave.

Figure 2A:
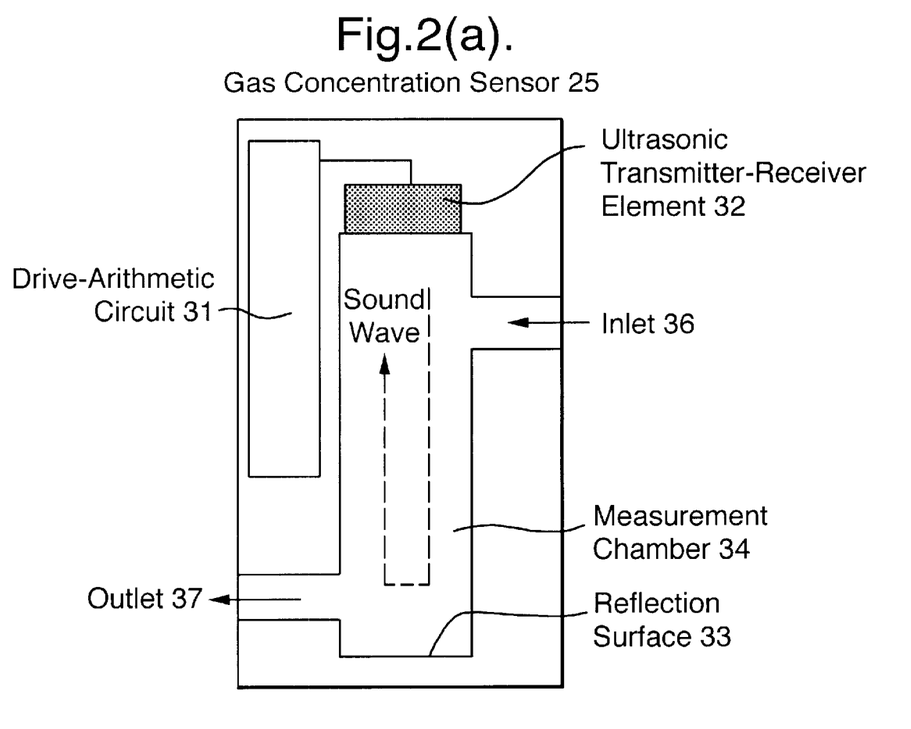
FIGS. 2(a) and (b) are views showing a gas concentration sensor, where (a) is an explanatory view showing the entire structure of the gas concentration sensor, and (b) is an explanatory view showing an ultrasonic transmitter-receiver element.

Specifically, as shown in FIG. 2, the gas concentration sensor 25 includes a drive-arithmetic circuit 31; an ultrasonic transmitter-receiver element (hereinafter referred to merely as an ultrasonic element) 32; a measurement chamber 34 into which intake air including vaporized fuel is introduced; a reflection surface 33 which is formed on one end portion of the measurement chamber 34 opposite the ultrasonic element 33 to be located a predetermined distance away from the ultrasonic element 32 and adapted to reflect an ultrasonic wave within the measurement chamber 34; an inflow hole (an inlet 36) for allowing inflow of intake air; and an outflow hole (an outlet 37) for allowing outflow of intake air.

Figure 2B:
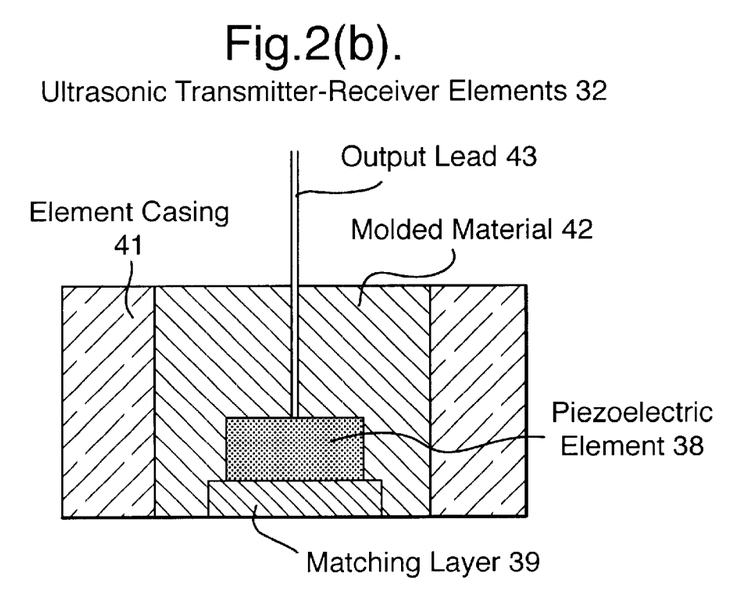

The ultrasonic element 32 includes a piezoelectric element 38 and a matching layer 39 bonded to the piezoelectric element 38. The piezoelectric element 38 and the matching layer 39 are fixed within an element casing 41 by means of a molded material 42. An output lead 43 is extended from the piezoelectric element 38 in order to output a sensor output from the piezoelectric element 38.

(2) Next, the configuration of the drive-arithmetic circuit 31 of the gas concentration sensor 25 will be described.

Figure 3:
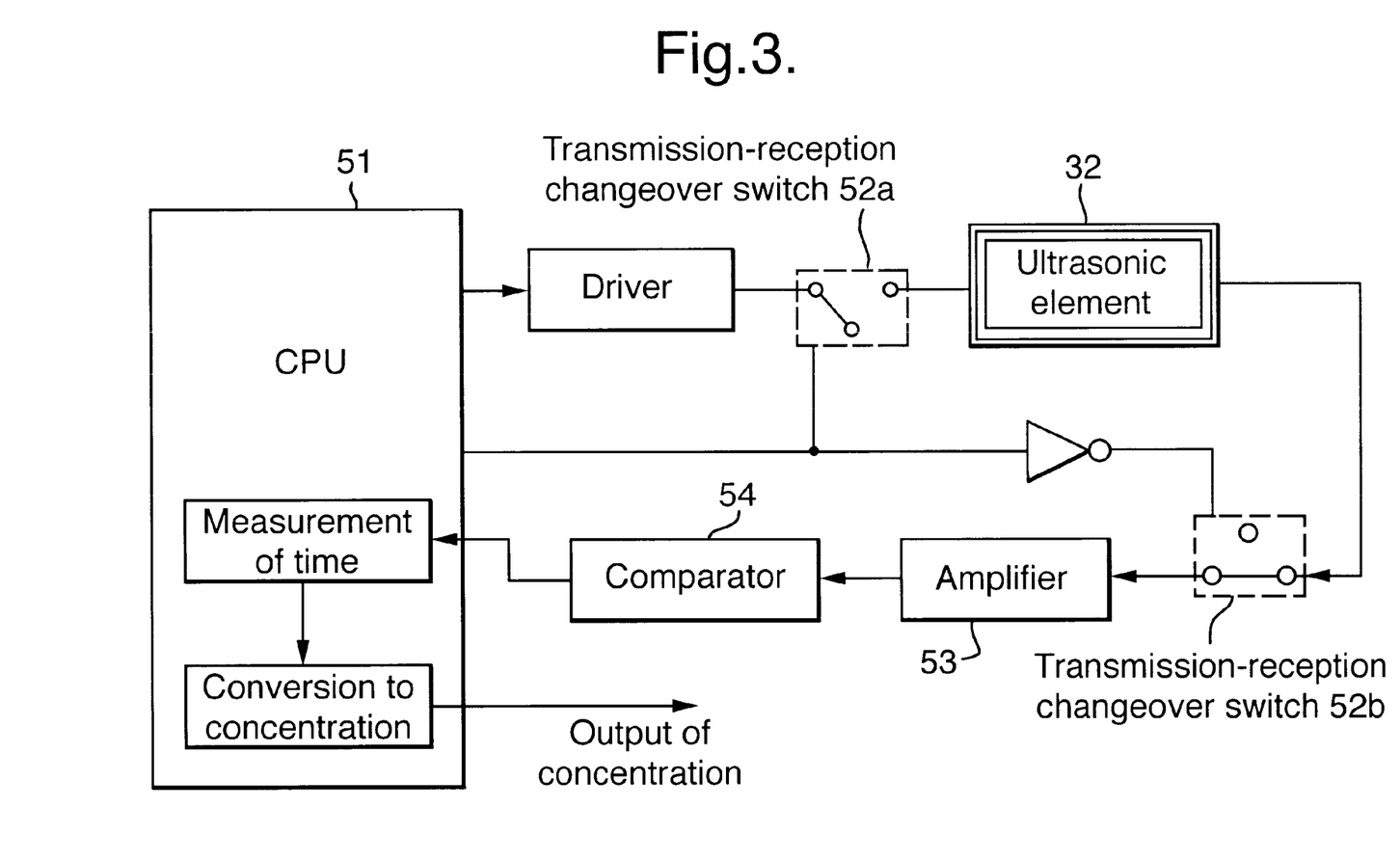
FIG. 3 is a block diagram showing the electrical configuration of the gas concentration sensor.

As shown in a block diagram of FIG. 3, a CPU (microcomputer) 51 is used to drive the gas concentration sensor 25 and to perform arithmetic operations. Transmission and reception of an ultrasonic wave is changed over to each other by means of transmission-reception changeover switches 52*a* and 52*b*.

At the time of transmission, voltage is applied to the ultrasonic element 32 by use of a driver, to thereby transmit an ultrasonic wave. At the time of reception, a waveform received by the ultrasonic element 32 undergoes predetermined amplification at an amplifier 53 and is then shape-corrected at a comparator 54. The thus-shape-corrected signal is input to the CPU 51. The CPU 51 measures propagation time by use of a timer and converts the measured propagation time into concentration through reference to a map. The CPU 51 outputs the obtained concentration data to an unillustrated display unit.

(3) Next, the basic principle of the gas concentration sensor 25 will be described.

For convenience of explanation, in FIG. 4, a transmitter 25*b* and a receiver 25*a* are shown as separate elements. However, in the present embodiment, the same element performs transmission and reception.

Figure 4A:
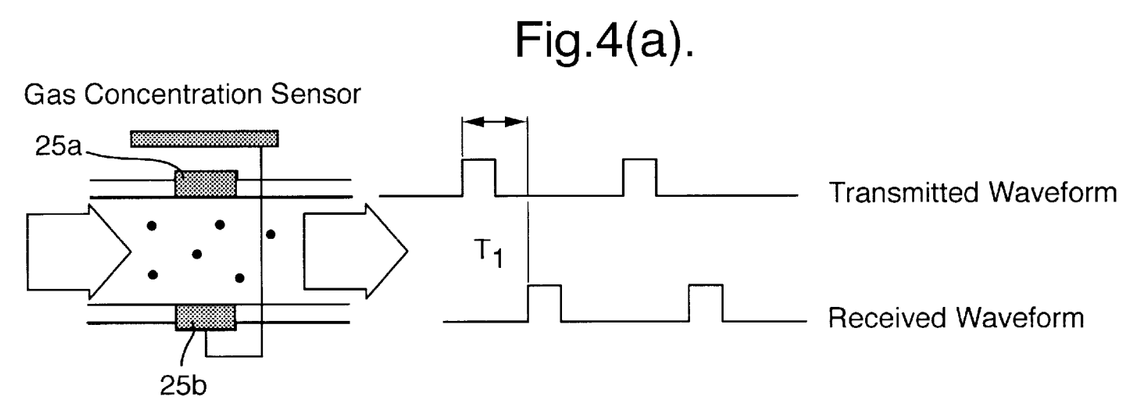
FIGS. 4(a) and (b) give explanatory views for explaining the basic principle of the gas concentration sensor.
Figure 4B:
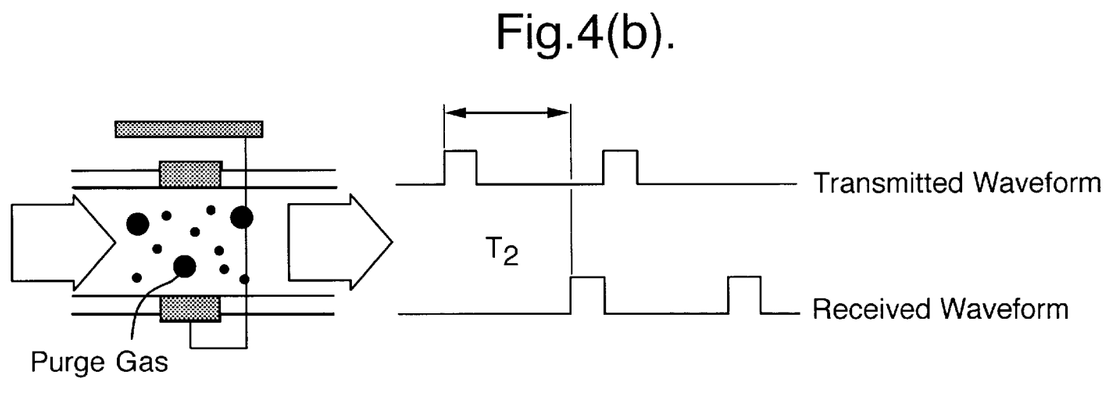

As shown in FIG. 4, in concentration measurement by use of the gas concentration sensor 25, an ultrasonic wave is transmitted from the transmitter 25*b*, and the ultrasonic wave is received by means of the receiver 25*a*. In this case, there is a time lag in propagation between a transmitted waveform and a received waveform according to, for example, purge gas concentration in intake air. For example, as shown in FIG. 4(*a*), when purge gas concentration is low, a propagation time T1, which is a time lag between the transmitted wave form and the received waveform, is short. By contrast, as shown in FIG. 4(*b*), when purge gas concentration is high, a propagation time T2 is long. Accordingly, through obtainment of a sensor output corresponding to propagation time, gas concentration can be determined.

Figure 5:
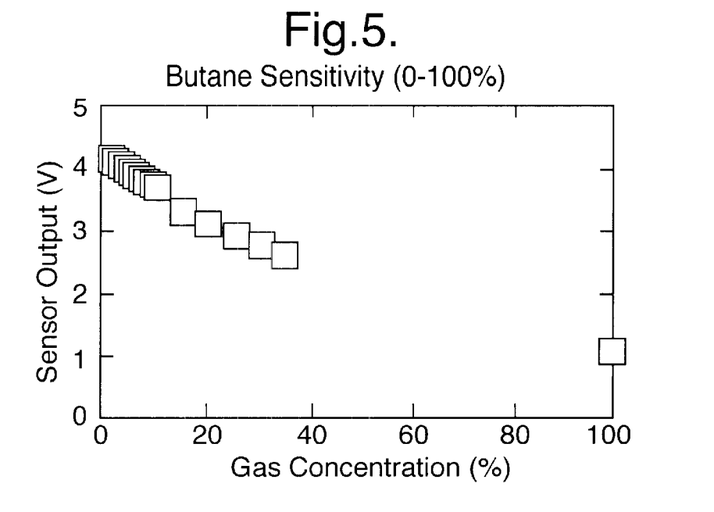
FIG. 5 is a graph showing the butane sensitivity in the case where the sensor accuracy is proper.

For example, measurement of gas concentration of butane, which is a main component of vaporized fuel, has revealed that a sensor output is substantially proportional to butane gas concentration as shown in FIG. 5. Accordingly, through obtainment of a sensor output, purge gas concentration can be determined from the obtained sensor output.

c) Next will be described an actual method of measuring vaporized fuel (purge gas) concentration by means of the gas concentration sensor 25 which operates according to the above-mentioned basic principle.

(1) First, an arithmetic expression example for calculating gas concentration from propagation time of an ultrasonic wave will be described.

Figure 6A:
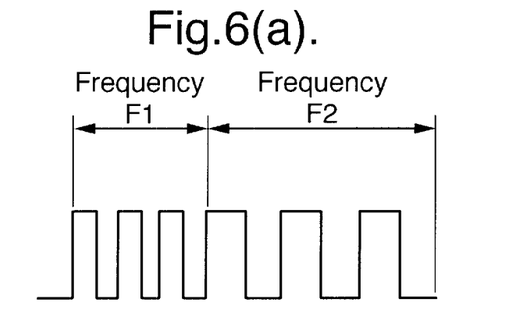
FIGS. 6(a) and (b) are explanatory views, wherein (a) is an explanatory view showing frequency modulation, and (b) is an explanatory view showing the distance between the sensor and the reflection surface.

In the present embodiment, as shown in FIG. 6(*a*), an ultrasonic wave which includes two kinds of frequency components, F1 and F2, is transmitted. That is, transmission frequency is modulated from F1 to F2.

In this case, since a received wave reflects the frequency modulation, arrival time is when a modulation point appears in the received wave. Through measurement of a time interval between frequency changeover points (for example, between a modulation point of the transmitted wave and that of the received wave), propagation time is obtained.

After propagation time is measured, the speed of sound C of an ultrasonic wave, which represents gas concentration, is calculated by use of expression (1) shown below.

Figure 6B:
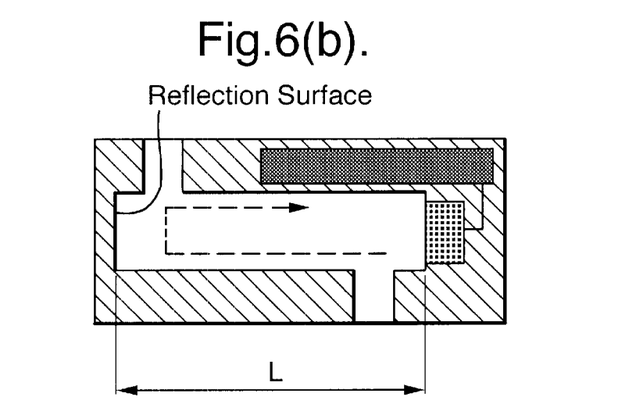

As shown in FIG. 6(*b*), a distance L between the outer surface of the ultrasonic element 32 (surface of a thin resin film affixed to the matching layer 39) and the reflection surface 33 is known. A propagation time T, which is a time interval required to propagate back and forth over the distance L, is measured. The known distance L and the measured propagation time T are substituted into the following expression (1) to thereby calculate the speed of sound C.

$$C=2L(\text{distance to propagate back and forth between element surface and reflection surface})/T \text{ (propagation time)} \quad (1)$$

Accordingly, when a sensor output (voltage) corresponding to the speed of sound C is detected, the gas concentration can be obtained through reference to a map as shown in FIG. 5.

(2) Next, the method of measuring gas concentration will be described with reference to examples of actual reflection waves.

FIG. 7 shows a transmitted/received waveform for the case where the speed of sound C is measured. When the ultrasonic element 32 transmits a frequency-modulated wave, the transmitted wave is reflected from the reflection surface 33. The reflection wave is detected as a first reflection wave by the ultrasonic element 32. The first reflection wave is reflected from the surface of the ultrasonic element 32 and is reflected again from the reflection surface 33. The reflected first reflection wave is detected again as a second reflection wave by the ultrasonic element 32. Subsequently, similar reflection is repeated. As a propagation distance increases, a reflection wave attenuates gradually.

Subsequently, upon elapse of a predetermined time after transmission of the first wave, in order to transmit the next wave, the transmission-reception changeover switches 52*a* and 52*b* are changed over. As a result, the next wave is transmitted, followed by repetition of similar processing.

A waveform input to the microcomputer (i.e., an output from the comparator) is as shown in FIG. 7. A time interval between frequency modulation points is measured. That is, a received wave is compared with a predetermined threshold level by the comparator to thereby be converted to a digital signal (high and low). The digital signal is input to the microcomputer. The microcomputer measures the rise time and fall time of the digital signal by means of an internal timer so as to identify a modulation point, thereby obtaining a time interval between modulation points.

Specifically, first, a first arrival time (first propagation time) T1 between a modulation point of the transmitted wave and a modulation point of the first reflection wave is measured. Also, a second arrival time T3 between the modulation point of the transmitted wave and a modulation point of the second reflection wave is measured. The first arrival time T1 is subtracted from the second arrival time T3 to thereby obtain the propagation time of the second reflection wave (second propagation time T2).

Accordingly, in the present embodiment, the thus-obtained propagation time T2 is used to determine gas concentration. The reason for using T2 is described below.

The first propagation time T1 varies due to, for example, time-course deterioration of the molded material 42 of the ultrasonic element 32. When the molded material 42 hardens or absorbs water to become heavier, the inertia of the piezoelectric element 38 varies. Conceivably, this inertia change not only affects the amplitude of the received waveform (sensitivity) but also causes a shift of a modulation point.

Specifically, for example, as seen from FIG. 8 which compares waveforms between a new sensor and an old sensor suffering time-course deterioration, the first reflection wave of the old sensor shows a decrease in the number of peaks and amplitude attenuation. As a result, a first propagation time T1' as determined by the old sensor becomes greater than a first propagation time T1 as determined by the new sensor. However, since the first reflection wave is reflected similarly from the surface of the ultrasonic element 32 and is then reflected from the reflection surface 33 to thereby become the second reflection wave, the second reflection wave is free from influence of time-course deterioration. Accordingly, a second propagation time T2 as determined by the new sensor becomes equal to a second propagation time T2' as determined by the old sensor.

Accordingly, through use of the second propagation time in calculating the speed of sound C, the speed of sound C can always be calculated properly without being susceptible to time-course deterioration.

Even when time-course deterioration is involved, since a modulation point of the first reflection wave and that of the second reflection wave are both shifted, use of the second propagation time cancels a shift of a modulation point derived from a time-course variation. Thus, even when a time-course variation is involved, propagation time can be measured properly.

In the present embodiment, the speed of sound C is calculated by use of the above-mentioned second propagation time to thereby obtain a sensor output corresponding to the calculated speed of sound C. A predetermined map as shown in FIG. 5 is referred to with respect to the obtained sensor output to thereby determine gas concentration.

A result similar to that obtained by the above-described method can be obtained by use of a method in which a time interval between a certain modulation point and the next modulation point is directly measured. Further, a portion of a waveform at a modulation point may suffer poor reproducibility at a certain threshold level setting of the comparator 54. Therefore, a modulation point may be used merely as an index point. A peak of the waveform located appropriately away from the modulation point may be used as an object of detection.

d) Next, a test example carried out by use of the gas concentration sensor 25 of the present embodiment will be described.

A car having a straight 6-cylinder, 2.0-liter engine was used as a test vehicle, and the engine was controlled such that the air-fuel ratio λ became 1±0.03.

Figure 9A:
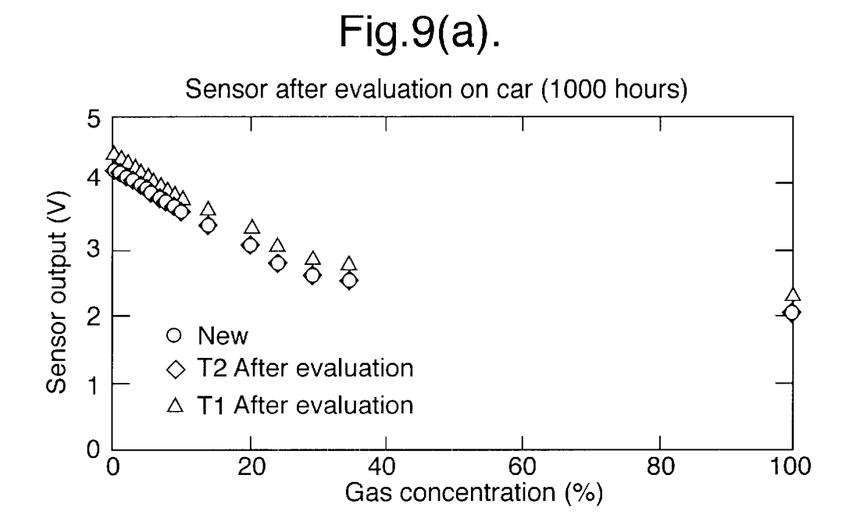
FIGS. 9(a) and (b) are graphs showing results of a test performed on a car, wherein (a) is a graph for a range up to a gas concentration of 100%, and (b) is a graph showing a range up to a gas concentration of 20% in an enlarged manner.
Figure 9B:
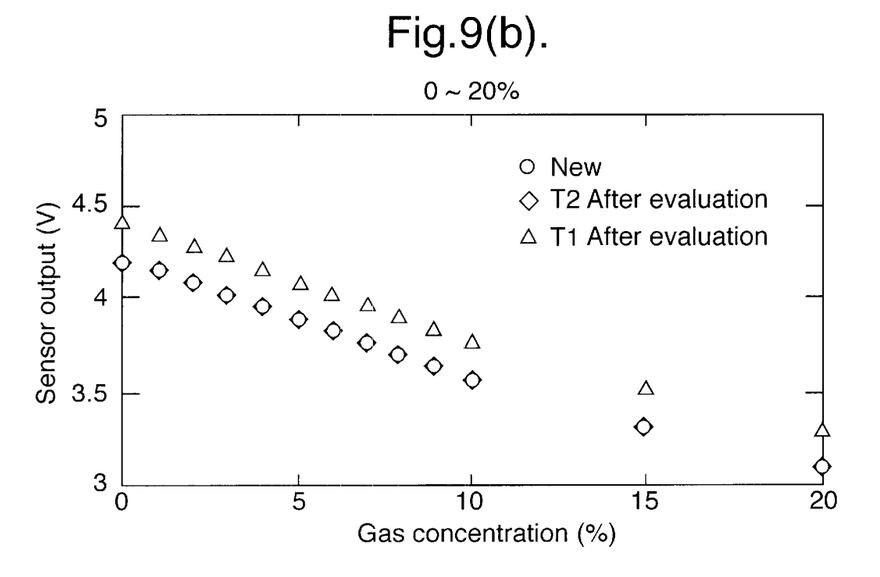

The test investigated an output of a new gas concentration sensor (using the first propagation time), an output of the sensor after elapse of 1000 hours on the test vehicle as determined on the basis of the first propagation time, and an output of the sensor after elapse of 1000 hours on the test vehicle as determined on the basis of the second propagation time. FIGS. 9(a) and 9(b) show test results, wherein FIG. 9(b) represents an enlargement of an area of FIG. 9(a) below a concentration of 20%.

As is apparent from FIGS. 9(a) and 9(b), in the case of the comparative example in which the first propagation time is used, due to an increase in the first propagation time, the sensor output increases as compared with that when the gas concentration sensor was new, so that an error is produced.

By contrast, in the case of the present embodiment in which the second propagation time is used, since the second propagation time remains unchanged, regardless of deterioration of the sensor, the sensor output is the same as that when the gas concentration sensor was new, which is preferred.

As described above, in the present embodiment, gas concentration is obtained on the basis of the second propagation time—which represents the propagation time of the second reflection wave and which is hardly affected by deterioration of the sensor. Therefore, precise concentration of vaporized fuel can always be obtained.

Accordingly, the amount of vaporized fuel to be supplied can be regulated accurately on the basis of the precise gas concentration, so that air-fuel ratio control and other controls can be performed accurately.

Second Embodiment

Next, a second embodiment of the present invention will be described.

Descriptions of portions identical with those of the first embodiment are omitted or simplified.

Figure 10A:
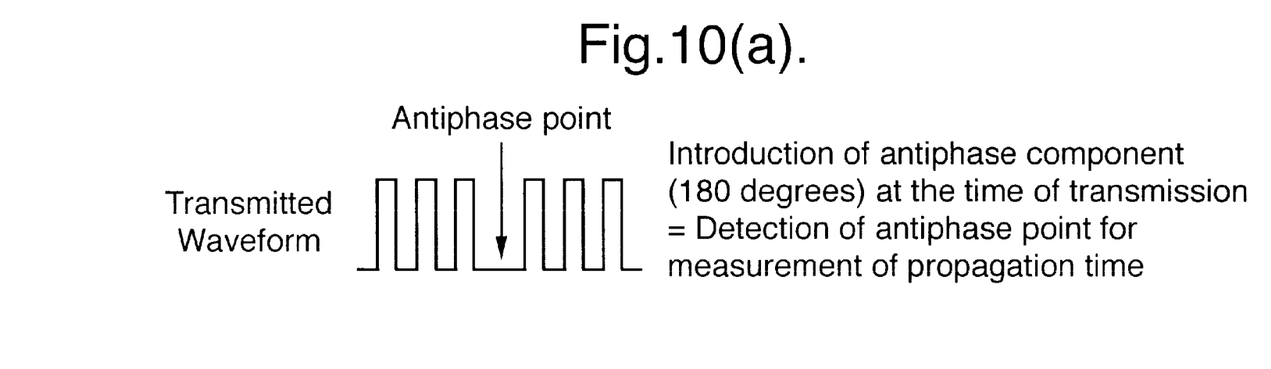
FIGS. 10(a) and (b) give explanatory views showing transmitted and received waveforms of an ultrasonic wave in a gas concentration sensor of the second embodiment.

In the present embodiment, when an ultrasonic wave is transmitted, as shown in FIG. 10(a), an antiphase component (180°) is introduced therein. Accordingly, no signal waveform appears at an antiphase point in the transmitted waveform.

Figure 10B:
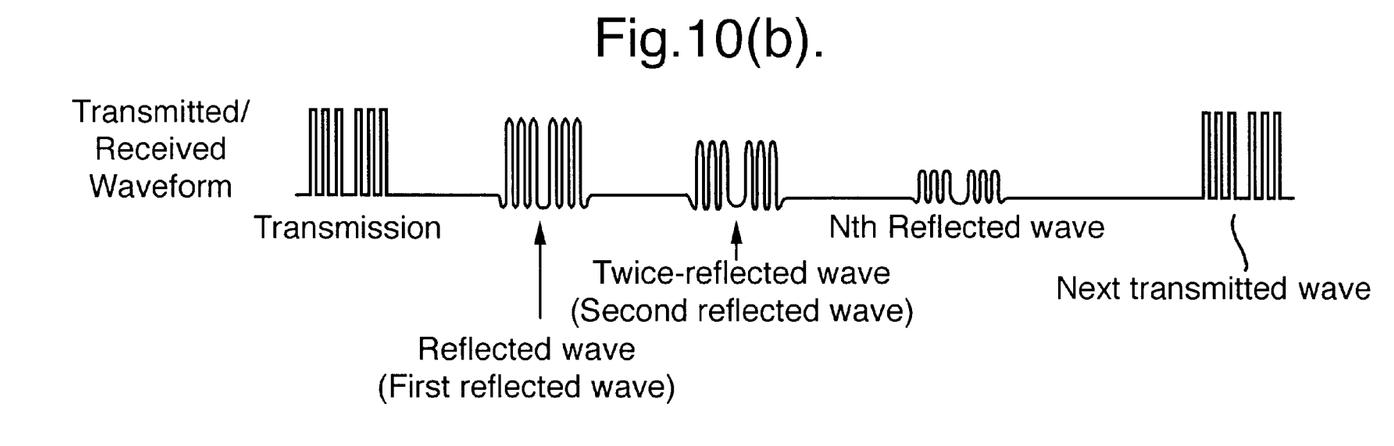

Thus, as shown in FIG. 10(b), a received wave; i.e., a reflected wave includes a point which corresponds to the antiphase point and at which no signal waveform appears.

Accordingly, when the propagation time is measured while the point at which the antiphase component was introduced is used as reference point, gas concentration can be measured without influence of variation in the sensor over time.

Specifically, the propagation time of the second reflection wave (second propagation time) can be obtained accurately through subtraction of the time at which the antiphase point of the first reflection wave appears from the time at which the antiphase point of the second reflection wave appears. Therefore, gas concentration can be measured on the basis of the second propagation time.

Third Embodiment

Next, a third embodiment of the present invention will be described.

Descriptions of portions identical with those of the first embodiment are omitted or simplified.

Figure 11A:
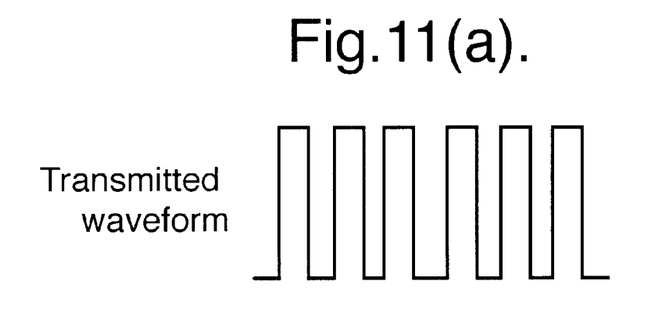
FIGS. 11(a) and (b) give explanatory views showing transmitted and received waveforms of an ultrasonic wave in a gas concentration sensor of the third embodiment.

In the present embodiment, as shown in FIG. 11(a), an ultrasonic wave of a predetermined frequency is transmitted without introduction of frequency modulation or an antiphase component.

Figure 11B:
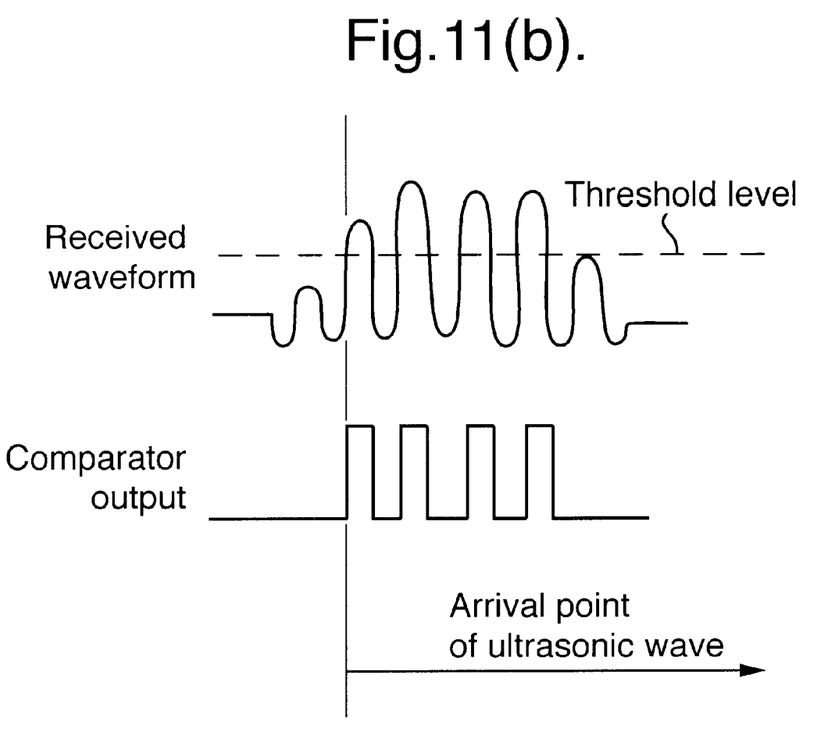

As a result, as shown in FIG. 11(b), the amplitude of the received wave changes with time. In the present embodiment, the amplitude of the received wave is compared with a predetermined threshold level, by use of the comparator 54. A point in time when the amplitude of the received wave reaches the predetermined threshold level is judged to be an arrival point (or arrival timing) of the ultrasonic wave.

Accordingly, when the propagation time is measured while the arrival point of the ultrasonic wave is used as reference point, gas concentration can be measured without influence of variation in the sensor over time.

Specifically, the propagation time of the second reflection wave (second propagation time) can be obtained accurately through subtraction of a time corresponding to the arrival point of the first reflection wave from a time corresponding to the arrival point of the second reflection wave. Therefore, gas concentration can be measured on the basis of the second propagation time.

The present invention has an advantage in that the structure of the sensor can be simplified as compared with the first and second embodiments, because introduction of frequency modulation or an antiphase component is unnecessary.

The present invention is not limited to the above-described embodiment and may be practiced in various manners without departing from the scope of the present invention.

For example, two ultrasonic elements may be disposed such that one element transmits ultrasonic waves and the other element received the ultrasonic waves.

As described above, in the gas concentration sensor of the present invention, an ultrasonic element transmits an ultrasonic wave toward a reflection surface so that ultrasonic wave reflects off the reflection surface to thereby become a first reflection wave, the ultrasonic element reflecting the first reflection wave so that the first reflection wave is again reflected off the reflection surface, and concentration of the specific gas is detected on the basis of a propagation time of a reflection wave other than the first reflection wave. Therefore, precise gas concentration can always be measured without influence of variation in the sensor over time and other causes.

Accordingly, the amount of a specific gas to be supplied can be regulated accurately on the basis of the precise concentration of the specific gas, so that air-fuel ratio control and other control measures can be performed accurately.

While the invention has been described in detail and with references to specific embodiments thereof, it will be apparent to one skilled in the art that various changes and modifications can be made therein without departing from the spirit and scope thereof.

This application is based on Japanese Patent Application No. Hei. 11-4286 filed Jan. 11, 1999 and is incorporated herein by reference.

What is claimed is:

1. A gas concentration sensor which detects the gas concentration of a specific gas, comprising:

a measurement chamber having a space into which the specific gas is introduced and having a reflection surface inside the chamber;

an ultrasonic element for transmitting an ultrasonic wave toward the reflection surface that is located inside the measurement chamber and at a predetermined distance away from the ultrasonic element; and a drive circuit for driving the ultrasonic element so as to transmit an ultrasonic wave having at least two frequency components;

wherein the transmitted ultrasonic wave propagates through the gas and reflects off the reflection surface to form first and second reflection waves, the first reflection wave being the transmitted ultrasonic wave reflected at the reflection surface, the ultrasonic element reflecting the first reflection wave toward the reflection surface, and the second reflection wave being the first reflection wave reflected at the reflection surface, wherein the concentration of the specific gas is determined on the basis of an arrival time difference between the first and second reflection waves reflected at the reflection surface and arriving at the ultrasonic element, and wherein the transmitted ultrasonic wave and the first and second reflection waves each has an antiphase component, and the arrival time difference is determined by measuring a time period between the antiphase component of the first reflection wave and the antiphase component of the second reflection wave.

2. The gas concentration sensor according to claim 1, wherein said specific gas is vaporized fuel for use with an internal combustion engine.

3. The gas concentration sensor according to claim 1, wherein said ultrasonic element comprises a piezoelectric element.

* * * * *